United States Patent [19]
Bazin et al.

[11] Patent Number: 6,133,573
[45] Date of Patent: Oct. 17, 2000

[54] METHOD AND DEVICE FOR DETERMINING A GAS VOLUME CONCENTRATION

[75] Inventors: Alain Bazin, Villejuif; François Grasdepot, Fontenay aux Roses, both of France; Juan Pedro Silveira, Madrid, Spain

[73] Assignee: Schlumberger Industries, S.A., Montrouge, France

[21] Appl. No.: 09/012,086

[22] Filed: Jan. 22, 1998

[30] Foreign Application Priority Data

Jan. 31, 1997 [FR] France ................................. 97 01198

[51] Int. Cl.⁷ .................................................. G01N 21/31
[52] U.S. Cl. ............................ 250/343; 356/437; 356/435
[58] Field of Search ............................. 250/343; 356/437, 356/435

[56] References Cited

U.S. PATENT DOCUMENTS

| | | | |
|---|---|---|---|
| 4,914,720 | 4/1990 | Knodle et al. | 250/343 |
| 4,998,017 | 3/1991 | Ryan et al. | 250/343 |
| 5,387,979 | 2/1995 | Brauer et al. | 356/435 |
| 5,429,805 | 7/1995 | Uno et al. | 250/343 |
| 5,506,685 | 4/1996 | Grasdepot | 356/437 |

*Primary Examiner*—Constantine Hannaher
*Assistant Examiner*—Andrew Israel
*Attorney, Agent, or Firm*—Leonard W. Pojunas

[57] ABSTRACT

A gas volume concentration is determined. An electromagnetic radiation is emitted (state 1) through the gas volume. The radiation is filtered by temporally modulating the spectral transmission of said filter so as to obtain a temporal modulation of the energy of the radiation transmitted by the gas volume and this filter. This temporally modulated energy is detected and a signal E is extracted from it, the signal particularly depending on the concentration of the gas. The component Eac(1) of the time-variable signal and the component Edc(1) of the signal, which is not a time-variable signal are isolated. A radiation stops is emitted (state 0), and the component Eac(0) and the component Edc(0) of the signal received by the detector are isolated. The terms Eac(1)-Eac(0) and Edc(1)-Edc(0) are calculated, and the ratio (Eac(1)-Eac(0))/(Edc(1)-Edc(0)) is formed which then solely depends on the gas concentration c. From this, c is deduced.

9 Claims, 3 Drawing Sheets

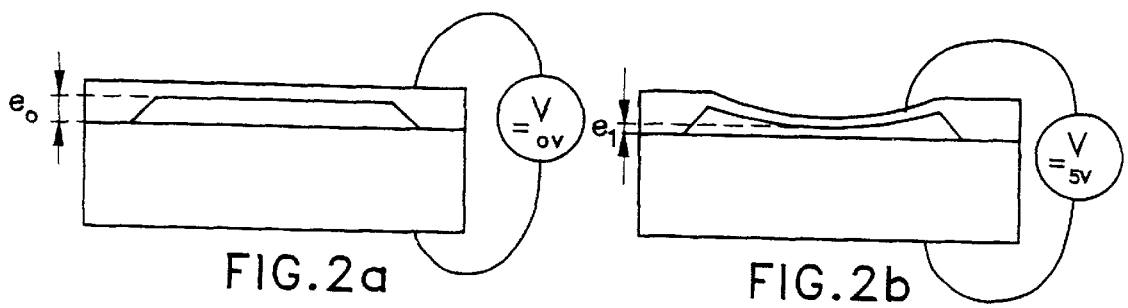
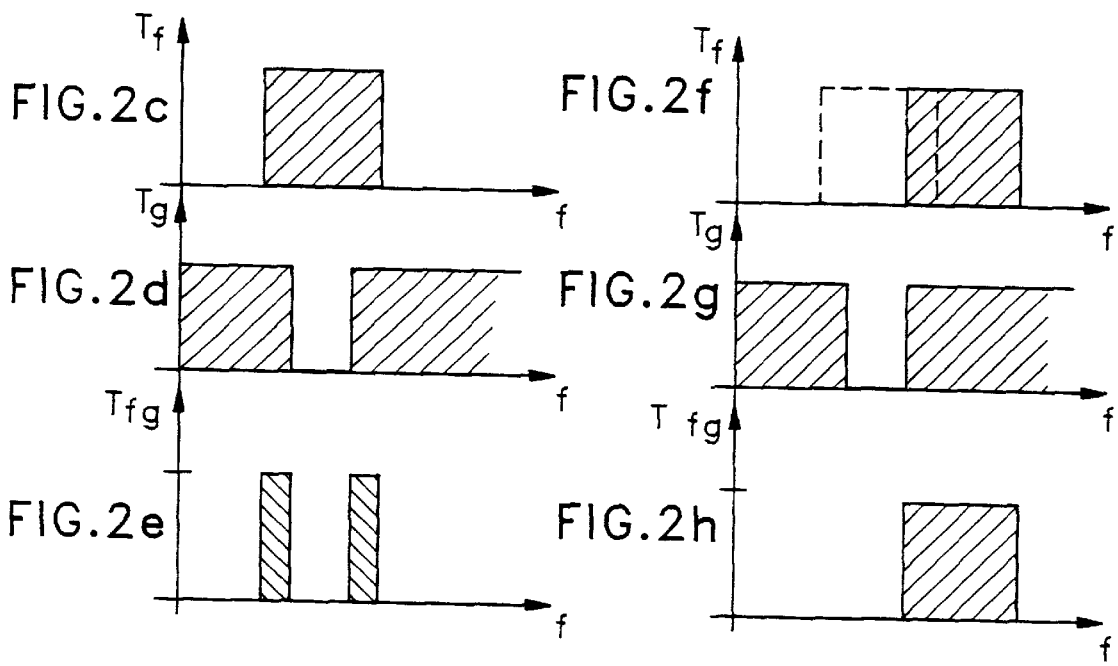
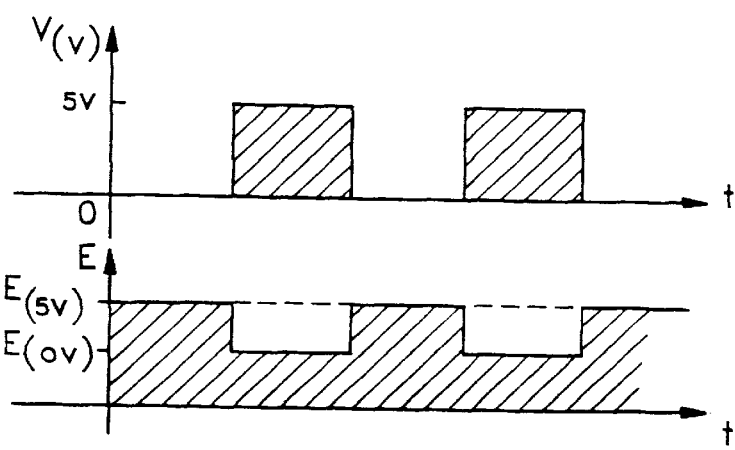

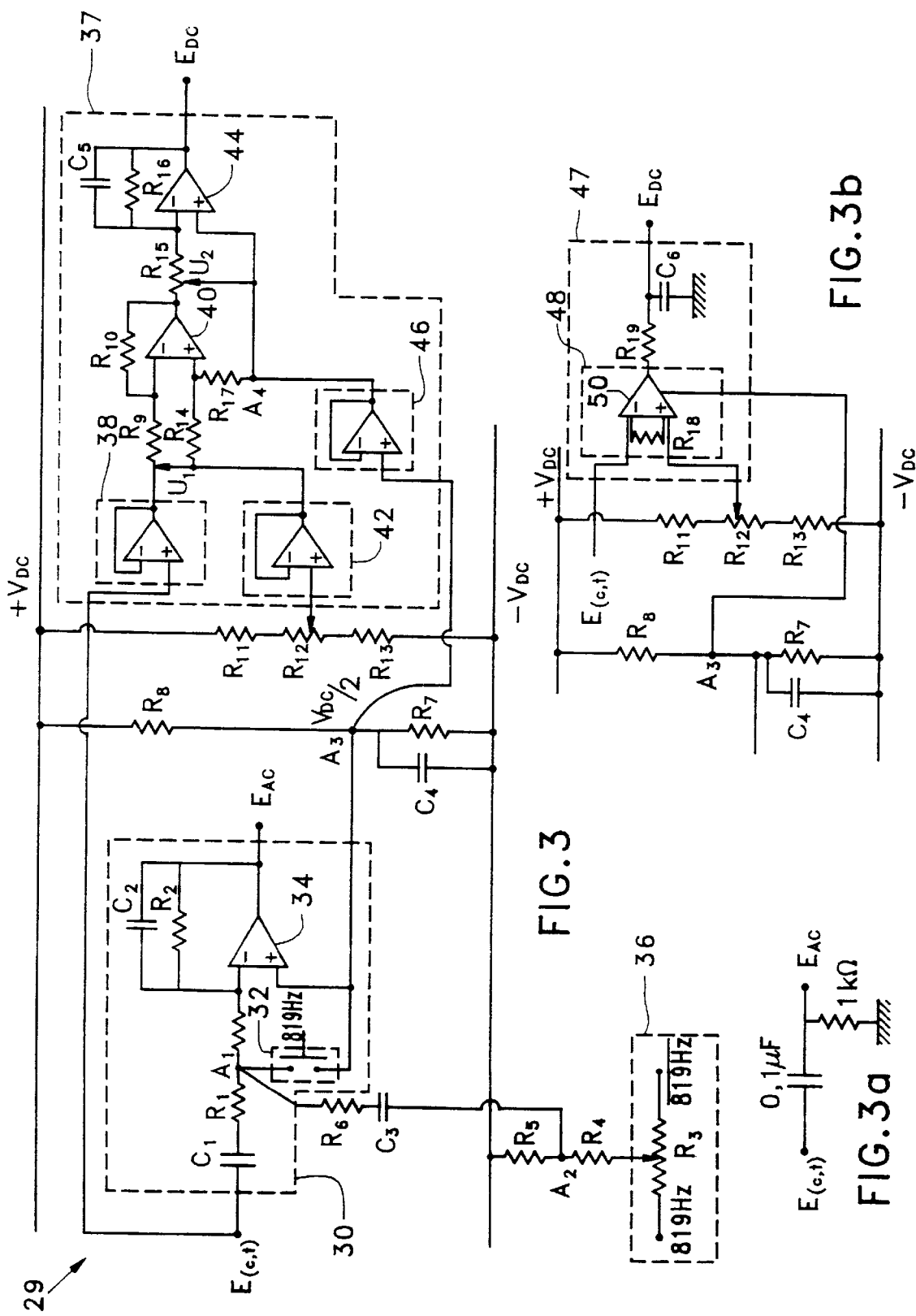

METHOD AND DEVICE FOR DETERMINING A GAS VOLUME CONCENTRATION

FIELD OF THE INVENTION

The invention concerns a method and device for determining a concentration of a gas volume.

BACKGROUND OF THE INVENTION

This device includes an electromagnetic radiation source, such as an optical source. For example, this source may be an infrared lamp emitting a radiation with a wavelength $\lambda 0$.

The device also includes a cell containing a gas volume with a given concentration. The radiation derived from the lamp traverses the cell and is selectively absorbed by the gas. At the cell outlet, the radiation has a spectral density modified by the presence of absorption peaks due to the lines of the gas.

A wavelength-tunable filter is adjusted to the wavelength $\lambda 0$ and is temporally modified so that its spectral transmission varies according to the time and wavelength. This modulated filter receives the radiation which has traversed the gas volume and in reply provides a temporary modulation of the energy of this radiation.

A detector, such as a bolometer, receives the energy transmitted by the filter, integrates as regards the entire spectral width of the received energy source and furnishes an average response which no longer depends on the wavelength $\lambda$ of the radiation, but more particularly on the concentration of the gas, this response being expressed as follows:

$$E(c,t)=[Sac(c,t)+Sdc(c)]P+Oac(t)+Odc.$$

The values of Sac(c,t) and Sdc respectively correspond to the temporal modulation and the mean value of the integral as regards the entire spectral region of the source from the energy balance between the source and the detector through the wavelength-tunable filter and the gas having a spectral absorption band concerning the region in question.

The term P is an unknown variable coefficient of optical losses which may take account of the dust covering the device in question.

The term Oac(t)+Odc is a zero shift, mainly due to the detector, and appears in the form of two terms respectively corresponding to a time-variable portion, Oac(t), and a non-time variable portion Odc.

Now, with this type of device, the influence of the optical losses coefficient P and the drifts of the detector make it impossible to reliably determine the gas concentration.

As a consequence, it would be very interesting to be able to make up for the optical losses coefficient P and the drifts of the detector with a view to obtaining the gas concentration more reliably.

SUMMARY OF THE INVENTION

The present invention concerns a method and device for determining the concentration of a gas and is easily able to attain this aim.

Thus, the present invention concerns a method for determining a concentration of a gas volume, wherein:

an electromagnetic radiation is emitted (state 1) through the gas volume,
said radiation is filtered by temporally modulating the spectral transmission of said filter so as to obtain a temporal modulation of the energy of the radiation transmitted by the gas volume and this filter,
this temporally modulated energy is detected and a signal E is extracted from it, said signal particularly depending on the concentration of the gas, wherein:
the component Eac(1) of the time-variable signal is isolated,
the component Edc(1) of the signal, which is not a time-variable signal, is isolated,
a radiation (state 0) stops being emitted, and
the component Eac(0) of the signal received by the detector is isolated,
the component Edc(0) of this signal is isolated,
the terms Eac(1)-Eac(0) and Edc(1)-Edc(0) are calculated,
the ratio (Eac(1)-Eac(0))/(Edc(1)-Edc(0)) is formed which then solely depends on the gas concentration c and c is deduced from this.

According to another characteristic of the invention, the electromagnetic radiation is of the optical type.

The present invention also concerns a device for determining a concentration of a gas volume including from upstream to downstream
at least one source emitting an electromagnetic radiation through the gas volume,
a wavelength-tunable filter and whose spectral transmission varies according to the wavelength and time,
a detector which, depending on the energy of the radiation having traversed the gas volume and the filter, produces a signal E dependent in particular on the gas concentration, wherein said device includes:
means for isolating the component Eac of the signal which varies with time respectively when the source is switched on (state 1) and not switched on (state 0), and
means for isolating the component Edc of the signal which does not vary with time when the source is switched on (state 1) and not switched on (state 0) respectively,
means for calculating the terms Eac(1)-Eac(0) and Edc(1) Edc(0) so as to form the ratio (Eac(1)-Eac(0))/(Edc(1) Edc(0) which is then solely dependent on the gas concentration and deduce c from this.

According to other characteristics of the invention
the means for isolating the component Eac of the signal are formed by a synchronous demodulation amplifier,
the means for isolating the component Eac of the signal are formed by a highpass filter,
the means for isolating the component Edc of the signal are formed by a differential amplifier followed by a lowpass filter and by impedance adapter circuits connected to the inversor and non-inversor inputs of said amplifier,
the means for isolating the component Edc of the signal are formed by an instrumentation differential amplifier followed by a lowpass filter,
the electromagnetic radiation is of the optical type,
the filter is a Fabry-Perot interferometer.

BRIEF DESCRIPTION OF THE DRAWINGS

Other characteristics and advantages shall appear from a reading of the following description given solely by way of non-restrictive example and with reference to the accompanying drawings on which:

FIGS. 2c–h represent the spectral transmissions of the filter, the gas and their product for two separate positions of the tunable filter, FIG. 2i represents the temporal modulation of the voltage applied to th filter, FIG. 2j indicates the speed of the energy E measured by the detector 18 according to the time involved, FIG. 3 is a view of the determination device of the invention, FIGS. 3a and 3b are partial views representing embodiment variants of the device of FIG. 3.

DETAILED DESCRIPTION OF THE PREFERRED EMBODIMENTS

Figure 1:
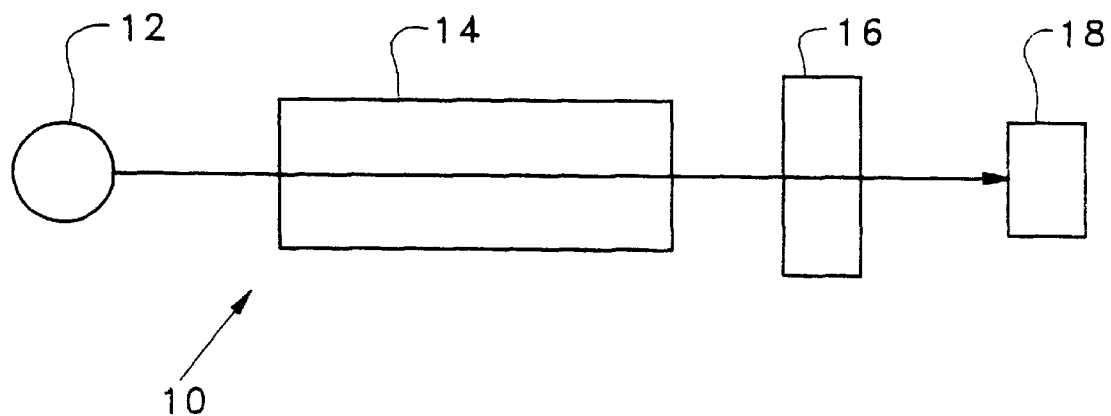
FIG. 1 is diagrammatic view of a device for determining a gas concentration.

As shown on FIG. 1 by the general reference 10, a device for determining the concentration of a gas, such as methane, includes an electromagnetic radiation source 12, such as an optical source.

This may be a spectral source of the incandescence or black body lamp type, and for example the lamp commercialized by the Royal Hamai company under the reference CNS-BP44X.

The source 12 is an infrared lamp emitting a radiation with a wavelength $\lambda 0 = 3.35$ μm, a wavelength which corresponds to one of the absorption lines of the methane. The source has a spectral distribution from a range of wavelengths extending from 2 to 4 μm.

The spectrum emitted by the lamp passes through a gas volume contained in a cell 14. The spectral transmission due to the gas has an absorption band within the spectral region of the lamp and thus depends on the concentration of the gas in the cell.

A wavelength-tunable filter 16 is temporally modulated, for example, by a signal with a frequency equal to 819Hz and the optical transmission of this filter varies according to the time and wavelength.

A detector 18, which may be a bolometer, receives the temporally modulated energy of the radiation derived from the lamp and having passed through the gas cell and the filter 16.

Figure 2:
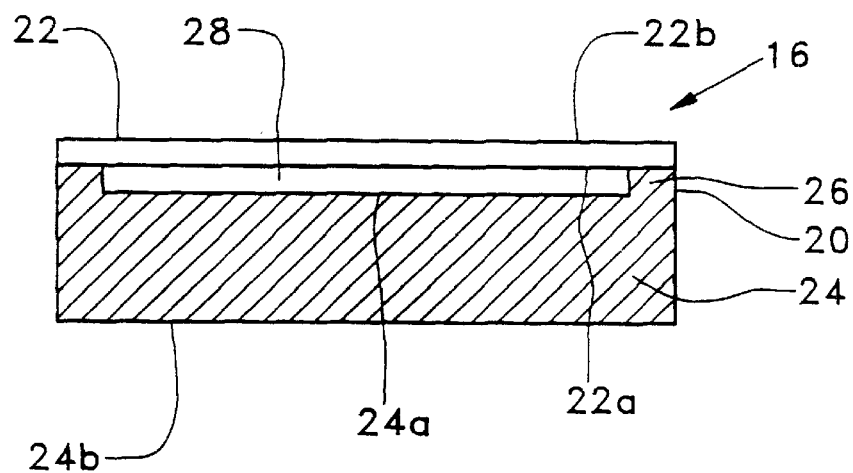
FIG. 2 is a cutaway diagrammatic view of an example of a filter used i the device of the invention.

As shown on FIG. 2, the filter 16 of FIG. 1 is formed of a body 20 which includes a first portion formed by an approximately circular membrane. The body also includes a second portion 24 forming a support with the general shape of a cylinder. The membrane 22 is fixed to the support 24 by means of a peripheral edge 26 of the support 24. The membrane 22 and the support have two surfaces 22a and 24a respectively opposite each other and collectively define a cavity 28 with a thickness eo. These surfaces are approximately flat and parallel to each other. For example, the cavity 28 contains a medium not having any spectral interference with the gas whose concentration is to be determined. The medium may be argon or another neutral gas or even a liquid. The cavity can also be placed under a vacuum. The membrane 22 is mobile with respect to the support 24 in a direction perpendicular to the pairing of opposing surfaces 22a and 24a. The optical radiation, which has a spectral distribution, is represented by a vertical arrow directed towards the membrane 22. The body 20 is transparent to the optical radiation selected and can be made of silicon. This filter can be obtained in the way indicated in the document EP 0 608 049 as regards the main production stages.

This filter is a Fabry Perot type interferometer whose initial thickness eo is adjusted according to the absorption line of the gas in question.

Thus, when the voltage applied to the filter is nil, the spectral transmission of the filter is for instance initially centered on the gas absorption line (thickness eo), as shown on FIG. 2a.

The transmission of the filter can be wavelength-tuned in another spectral position (FIG. 2b) (thickness e1) by applying a voltage temporally modulated to the frequency of 819 Hz between two extreme values corresponding to these two positions.

FIGS. 2c–e (resp. 2d–h) respectively show the spectral frequency transmission curves of the filter 16 (FIG. 2c, resp. 2f), the gas volume 14 (FIG. 2d, resp. 2g) and the product of said spectral transmissions (FIG. 2e, resp. 2h) for the position of the filter indicated on FIG. 2a (resp. 2b).

As represented on FIGS. 2c and 2d, the spectral transmission of the filter is tuned to the gas absorption band.

FIG. 2f indicates by the dotted line the spectral transmission of the filter prior to movement of the mobile membrane, as illustrated on FIG. 2c.

FIG. 2i represents the temporal variations of the voltage applied to the filter 16 whose spectral transmissions vary between the one indicated on FIG. 2c (at 0 V) and that of FIG. 2f (5 V), and FIG. 2j represents the temporal values of the value E measured by the detector 18.

A frequency generator (not shown on the figures) delivers from a quartz clock with a frequency equal to 32 kHz a square signal with a frequency equal to 819 Hz obtained respectively by dividing the signal of the master clock at 32 kHz by 10 and 4.

The detector 18 and its load resistor (not shown) are fed by a d.c. voltage+Vdc (e.g.+5 V) and the detector delivers at the output the energy E(c,t) expressed as follows:

$$E(c,t) = [Sac(c,t) + Sdc(c)] \, iP + Oac(t) + Odc$$

where c denotes the gas concentration,

Sac and Sdc respectively correspond to the temporal modulation and the mean value of the integral as regards the entire spectral region of the source of the energy balance between the source 12 and the detector 18 through the wavelength-tunable filter 16 and the gas cell 14, i is a Boolean parameter worth 1 if the source 12 is switched on and 0 if the source is switched off, P is an unknown coefficient of optical losses which takes accounts of the dust covering of the device in question, Oac(t)+Odc is a zero shift mainly due to the detector 18 and which appears in the form of two terms respectively corresponding to a time-variable portion Oac(t) and a non time-variable portion Odc.

The signal E(c,t) is represented on the left portion of FIG. 3 which shows a portion 29 of the device 10 of the invention for determining the gas concentration.

This figure describes means able to respectively isolate those components which vary with the time Eac and not varying with the time Edc of the signal E(c,t). The means able to isolate the component Eac of the signal E(c,t) may be made up of a synchronous demodulation amplifier 30.

The synchronous demodulation amplifier 30 includes at the input a capacitor C1 stopping the non-time varying signals, as well as a resistor R1. A switch 32 controlled by the synchronization frequency of the filter 16 (819 Hz) can be embodied by a series 4066 CMOS circuit and by modulating the signal E(c,t), this makes it possible to have the component Eac of this signal appear at the output of the differential amplifier 34.

A lowpass filter formed of a resistor R2 in parallel with a capacitor C2 is placed between the invertor input and the output of the amplifier 34 so as to filter the residue of the demodulation operation.

As a variant of the mounting described above, should the signal derived from the detector be scarcely affected by the noise, the means for isolating the component Eac of the signal E(c,t) can also be formed more simply by a conventional highpass filter made up of a capacitor with a value equal to 0.1 $\mu$F and a resistor with a value equal to 1 k$\Omega$, as represented on FIG. 3a.

So as to cancel the shift of the zero produced by the modulator in the absence of any energy received by the detector 18, a potentiometric assembly 36 is used and constituted by a variable resistor R3 receiving at its terminals the signal at 819 Hz and conversely.

By moving the cursor to the resistor R3, it is possible to adjust the shift of zero, thus adjusting the amplitude and phase of the shift signal to be injected onto the point A1.

The assembly constituted by the resistors R4 and R5 in series in which the resistor R5 is connected to the voltage source −Vdc forms an attenuator which is used to refine the zero adjustment.

A capacitor C3 in series with a resistor R6 connects the point A2 situated between the resistors R4 and R5 and the point A1 and forms a circuit for injecting the shift signal which stops the continuous component of this signal.

The component Eac evolves with respect to a reference point A3 which constitutes a dummy mass. The voltage at this point with respect to the mass is Vdc/2.

A capacitor C4 connected at one extremity to the voltage source −Vdc and at the opposing extremity to the point A3 and the equivalent resistance of the dividing bridge R7, R8 creates an uncoupling of the noise derived from the switch 32 so that this noise does not occur at the output of the amplifier 34.

Means 37 isolate the component Edc from the signal E(c,t) which does not vary with the time, said means being described as follows.

The signal E(c,t) derived from the detector 18 is sent onto an impedance adapter circuit 38 embodied by a differential amplifier used in a tracker type mounting able to therefore reduce the impedance offered to said signal E(c,t).

A resistor R9 connects the output of the circuit 38 to the invertor input of a differential amplifier 40 and a resistor R10 connects said invertor input to the output of this amplifier.

Three resistors R11, R12 and R13 are mounted in series between the respective voltage sources +Vdc, −Vdc.

The resistor R12 is a variable resistor and, via a movement of the cursor of the embodied potentiometric mounting, it is possible to adjust the shift of the zero of the signal Edc to be obtained.

The resistors R11 and R13 surrounding the resistor R12 are used to refine the zero adjustment.

Another impedance adapter circuit 42 embodied by a differential amplifier is used in a tracker mounting, the non-invertor input of said amplifier being connected to the variable resistor R12.

The aim of this circuit 42 is to reduce the impedance of the dividing bridge R11, R12, R13 viewed from the cursor of the potentiometer R12.

The output of the circuit 42 is connected to the input of the non-invertor input of the amplifier 40 by means of a resistor R14.

The output of the amplifier 40 is connected to the invertor input of an operational amplifier 44 used to increase the level of the output signal Edc.

A lowpass filter formed of a capacitor C5 in parallel with a resistor R16 is mounted between the invertor input of the amplifier 44 and its output so as to filter the noise present in the signal Edc.

An impedance adapter circuit 46 embodied by a differential amplifier used in a tracking mounting is provided so that the non-invertor input of said amplifier is connected to the point A3 and the output of the latter is connected to the point A4. A resistor R17 is placed between the point A4 and the non-invertor input of the amplifier 44.

This circuit 46 is able to avoid reinjecting currents onto the reference point A3 which would introduce a disturbance in measuring the component Eac.

The voltage U1 applied between these two branches respectively arriving on the invertor and non-invertor inputs of the amplifier 40 is found again at the output of this amplifier between the branch bearing the resistor R15 and the point A4.

This is rendered possible by virtue of the mating of the resistors R9, R14, R10 and R17.

Thus, the component Edc of the signal E(c,t), that is a non-time varying signal, is obtained at the outlet of the mounting 37.

A variant represented on FIG. 3b shows means 47 for isolating the component Edc from the signal E(c,t), said means being formed of an instrumentation differential amplifier 46 constituted by a differential amplifier 50 equipped between its two inputs with a resistor R18 receiving on its invertor input the signal E(c,t) and having its non-invertor input connected to the potentiometric mounting using the variable resistor R12.

This amplifier is fed by the voltage taken up at the point A3 (Vdc/2) and by its nature has a high common mode rejection rate.

This amplifier may be the one commercialized by the ANALOG DEVICES company under the reference AD260.

Provided at the output of this amplifier are a conventional lowpass filter constituted by a resistor R19 and a capacitor C6 so as to filter the undesired time-variable components.

In the continuation of the description, the method of the invention for determining the gas concentration shall be described as follows.

When the optical radiation source 12 is switched off, the Boolean parameter i in the expression of the energy received by the detector 18 is worth 0 and the energy E(c,0) is then equal to the term Oac(0)+Odc corresponding to the drift of the detector.

By means of the means 30 and 37 described previously with reference to FIGS. 3 and 3a–b, the time-variable components Eac and the non time-variable components Edc can be separated.

Thus, the means 30 deliver at the output the component Eac(0) which is equal to the portion Oac of the term Oac(0)+Odc in the absence of any lighting.

This value is a constant which is stored in a live memory (not shown on the figures). The means 37 provide at the output the component Edc(0) which is equal to the portion Odc of the term Odc(0)+Odc in the absence of any lighting.

Then the source 12 is switched on, the Boolean parameter i is then worth 1 and the energy E(c,t) is equal to the term [Sac(c,t)+Sdc(c)] P+Oac(t)+Odc.

It is proper to note that the method of the invention is applicable irrespective of the direction of change of the state of the parameter i (moving from the state 0 to 1 or 1 to 0)

The means 30 and 37 are able to respectively isolate the components Eac(1) and Edc (1).

$$Eac(1l)=sac(c).P+Oac(0)$$

let $Eac(1)=Sac(c).P+Eac(0)$ and $Edc(1)=Sdc(c).P+Odc$ let $Edc(1)=Sdc(c).P+Edc(0).$ Similarly, the values Eac(1) and Edc(1) are stored in a live memory (not shown).

It is proper to note that the ratio Eac/Edc is unstable under the effect of two influences the influence of optical losses P including long-term changes, and the influence of the drift of the terms Oac(t) and Odc with the environment parameters, such as the temperature and whose changes take place over a shorter period of time.

Accordingly, for the method of the invention to be applicable, it is essential that the passage from the off state (0) to the state (1) and the various stages for measuring the values Eac(0), Edc(0), Eac(1) and Edc(1) are carried out in a sufficiently short period of time prior to the period of variations of the ratio Eac/Edc.

A known type of microprocessor calculates the terms Eac(1)-Eac(0) and Edc(1)-Edc(0) and carries out the ratio of these terms and gives:

$$R(c)=[Eac(1)-Eac(0).]/[Edc(1)-Edc(0).]=Sac(c)/sdc(c)$$

R(c) is therefore a function which depends solely on the gas concentration c.

By firstly carrying out a calibration of R(c) for different values of the concentration c, by means of linear interpolation, the value of the concentration c of the gas is deduced on the basis of the determined value for R(c).

The function R(c) is independent of the losses on the optical path (dust, etc) and zero shifts which are inevitable in the measuring chain. The embodiment of the device for determining the mean and long term concentration c of a stable gas (gas detector) is therefore possible by determining c in the way described below.

So as to obtain the best results, it is preferable to suitably select and size the tunable filter 16 and its modulation.

What is claimed is:

1. A method for determining a gas volume concentration according to which:

an electromagnetic radiation is emitted (state 1) through the gas volume, said radiation is filtered by temporally modulating the spectral transmission of a filter so as to obtain a temporal modulation of the energy of the radiation transmitted by the gas volume and this filter, this temporally modulated energy is detected and extracted from it is a signal E depending in particular on the gas concentration, wherein:

the component Eac(1) of the time-variable signal is isolated, the component Edc(1) of the signal, which is not a time-variable signal, is isolated, a radiation (state 0) stops being emitted, and the component Eac(0) of the signal received by the detector is isolated, the component Edc(0) of this signal is isolated, the terms Eac(1)-Eac(0) and Edc(1)-Edc(0) are calculated, the ratio (Eac(1)-Eac(0))/(Edc(1)-Edc(0)) is formed which then solely depends on the gas concentration c and c is deduced from this.

2. A method according to claim 1 according to which the electromagnetic radiation is of the optical type.

3. A device for determining a gas volume concentration and including from upstream to downstream:

at least one source emitting an electromagnetic radiation through the gas volume, a wavelength-tunable filter and whose spectral transmission varies according to the wavelength and time, a detector which, according to the energy of the radiation having traversed the gas volume and the filter, produces a signal E dependent in particular on the gas concentration, wherein said device includes:

means for isolating the component Eac of the signal which varies with time respectively when the source is switched on (state 1) and switched off (state 0), and means for isolating the component Edc of the signal which does not vary with time when the source is switched on (state 1) and switched off (state 0) respectively, means for calculating the terms Eac(1)-Eac(0) and Edc(1) Edc(0) so as to form the ratio (Eac(1)-Eac(0))/(Edc(1) Edc(0) which is then solely dependent on the gas concentration and c can therefore be deduced.

4. A device according to claim 3, wherein the means for isolating the component Eac of the signal are formed by a synchronous demodulation amplifier.

5. A device according to claim 3, wherein the means for isolating the component Eac of the signal are formed by a highpass filter.

6. A device according to claim 3, wherein the means for isolating the component Edc of the signal are formed by a differential amplifier followed by a lowpass filter and by impedance adapter circuits connected to the invertor and non-invertor inputs of said amplifier.

7. A device according to claim 3, wherein the means for isolating the component Edc of the signal are formed of an instrumentation differential amplifier followed by a lowpass filter.

8. A device according to claim 3, wherein the electromagnetic radiation is of the optical type.

9. A device according to claim 3, wherein the filter is a Fabry-Perot interferometer.

* * * * *